United States Patent

Cho et al.

[11] Patent Number: 5,475,311
[45] Date of Patent: Dec. 12, 1995

[54] IONIZATION GAS ANALYZER AND METHOD

[75] Inventors: Frederick Y. Cho, Higley; Eric S. Johnson, Scottsdale; Joseph W. Walsh, Mesa, all of Ariz.

[73] Assignee: Motorola, Inc., Schaumburg, Ill.

[21] Appl. No.: 237,706

[22] Filed: May 3, 1994

[51] Int. Cl.$^6$ ............................ G01N 27/62; G01N 27/70
[52] U.S. Cl. ............................................ 324/464; 340/632
[58] Field of Search ........................... 324/459, 464–466; 340/629, 632; 73/23.2, 23.31, 23.35, 28.02

[56] References Cited

U.S. PATENT DOCUMENTS

| | | | |
|---|---|---|---|
| 3,559,049 | 1/1971 | Liebermann et al. | 324/464 |
| 3,728,615 | 4/1973 | Hill et al. | 324/464 |
| 5,066,023 | 11/1991 | Ma | 324/464 X |
| 5,281,816 | 1/1994 | Jacobson et al. | 340/632 X |

Primary Examiner—Gerard R. Strecker
Attorney, Agent, or Firm—Jeffrey D. Nehr

[57] ABSTRACT

An ionization gas analyzer system includes an ionization chamber including ionization electrodes contained therein. The ionization chamber contains a test gas or gas mixture. A high voltage generator is coupled to the electrodes and provides variable high voltage pulses to the ionization electrodes. An ionization voltage analyzer is coupled to the ionization chamber and receives ionization voltage information from the plurality of ionization electrodes in response to the variable high voltages pulses. The ionization voltage analyzer produces a gas code identifier in response to the plurality of ionization voltages by defining a code based on which of the ionization voltages exceed an arbitrarily established reference level ionization voltage. A single ionization electrode system can be used to determine a concentration of a particular gas.

23 Claims, 4 Drawing Sheets

IONIZATION GAS ANALYZER AND METHOD

FIELD OF THE INVENTION

This invention relates in general to identifying gases, and in particular to identifying gases by characteristic ionization voltages.

BACKGROUND OF THE INVENTION

The identification of constituent gases in the emissions of internal combustion engines is increasingly important as environmental awareness and air pollution prevention are emphasized. Complete engine control systems are moving toward on-vehicle exhaust monitoring systems that, for example, are capable of checking catalytic converter performance. Along with potential application in literally hundreds of millions of private automobiles, such monitoring systems are desirable for public transportation vehicles such as buses, as well as police, fire, and ambulance vehicles, and a myriad of military applications.

Methods and systems for identifying constituent gases in a mixture include using gas chromatography, mass spectrometry, and cyclotron resonance. In general, these methods use extensive hardware in nonportable systems. Typically, these systems are expensive and difficult to operate. Such systems are also not generally suitable for use in a high temperature environment (greater than 700 degrees Celsius) and over a large range of pressure (0 to greater than $1.01 \times 10^5$ Pa (1 atmosphere)) such as that which may be encountered in a typical exhaust gas monitoring environment.

Thus, what is needed is a relatively simple, inexpensive, easy to operate portable gas ionization method and apparatus which can withstand high temperature and pressure. Such a system would be suitable for implementation as an on-board exhaust gas analyzer to provide exhaust gas analysis as part of a complete engine control system. It is also desirable that such a system and method be generally applicable to diverse applications such as drug control, breath analysis for health care purposes, and other applications.

DETAILED DESCRIPTION OF THE PREFERRED EMBODIMENT

Figure 1:
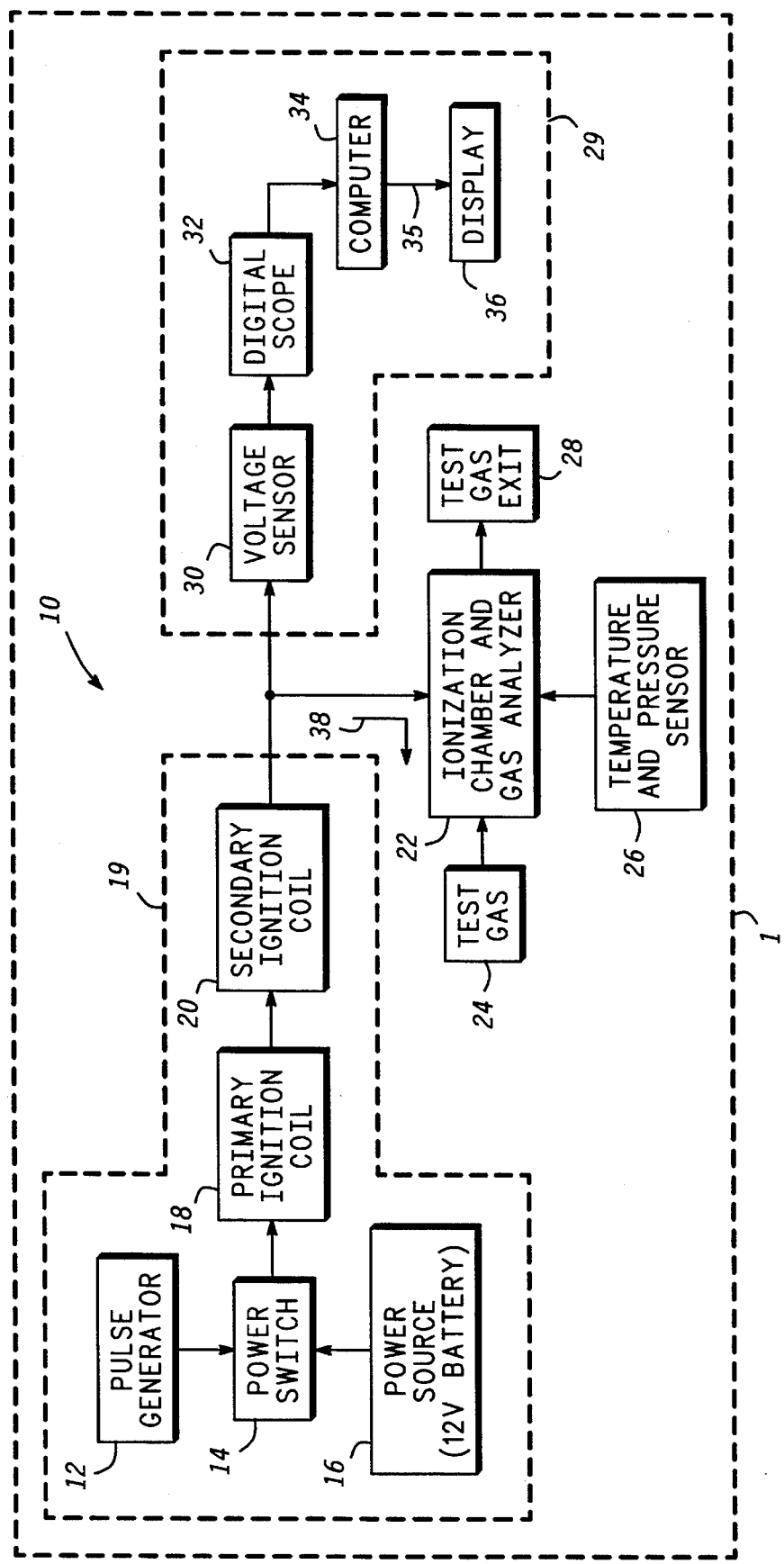
In FIG. 1, there is shown an ionization gas analyzer system and method in accordance with a preferred embodiment of the invention.

In FIG. 1, there is shown an ionization gas analyzer system 10 in accordance with a preferred embodiment of the invention. There are many possible implementations and uses for the ionization gas analyzer system 10, and one such application is shown in FIG. 1 where the ionization gas analyzer system 10 is shown as included within motor vehicle 1 as an exhaust gas analyzer.

The gas analyzer system 10 in FIG. 1 comprises a power source (e.g., a 12 volt (V) battery) 16 coupled to a power switch 14. A pulse generator 12 coupled to the power switch provides a pulse to a primary ignition coil 18. The primary ignition coil 18 is coupled to a secondary ignition coil 20 which outputs a stepped up high voltage pulse 38 in response to the input of the pulse to the primary ignition coil 18. The high voltage generating method and apparatus can include a typical power source 16, such as a vehicle battery in an automobile, and typical voltage step up apparatus, such as an automobile coil comprising the primary ignition coil 18 and the secondary ignition coil 20. The combination of power source 16, power switch 14, pulse generator 12, primary ignition coil 18 and secondary ignition coil 20 is shown in FIG. 1 as high voltage generator 19.

The high voltage pulse 38 from the secondary ignition coil 20 is monitored using voltage sensor 30 coupled to the secondary ignition coil 20. The high voltage pulse 38 is variable and controllable, based on the pulse generator 12 input and the primary ignition coil 18 and secondary ignition coil 20 configuration. The voltage sensor 30 is coupled to a digital scope 32, which is in turn coupled to a computer 34. Computer 34 is coupled to display 36 in the preferred embodiment of the invention. The voltage sensor 30, the digital scope 32, the computer 34, and the display 36, shown in combination as ionization voltage analyzer 29, allow the ionization gas analyzer system and an operator to monitor the high voltage pulse 38 to the ionization gas analyzer system and method. The ionization voltage analyzer 29 also monitors the ionization voltage for any particular test gas 24 or electrode set (described below in the description of FIG. 2). (As used herein, the term ionization voltage denotes the spark voltage.) In addition, the computer 34 includes an analysis program which correlates ionization voltages to a calibrated look-up table to provide the function of identifying the test gas 24 mixture as gas code identifier 35. Gas code identifier 35 and other output of the computer 34 can be shown on display 36. An application specific integrated circuit (ASIC) can be used to replace the digital scope 32 and computer 34.

Test gas 24 can be introduced into ionization chamber and gas analyzer 22 in FIG. 1. After testing, the gas is removed via test gas exit 28. An optional temperature and pressure sensor 26 coupled to the ionization chamber and gas analyzer 22 can provide the system or an operator with temperature and pressure information within the ionization chamber and gas analyzer 22.

Figure 2:
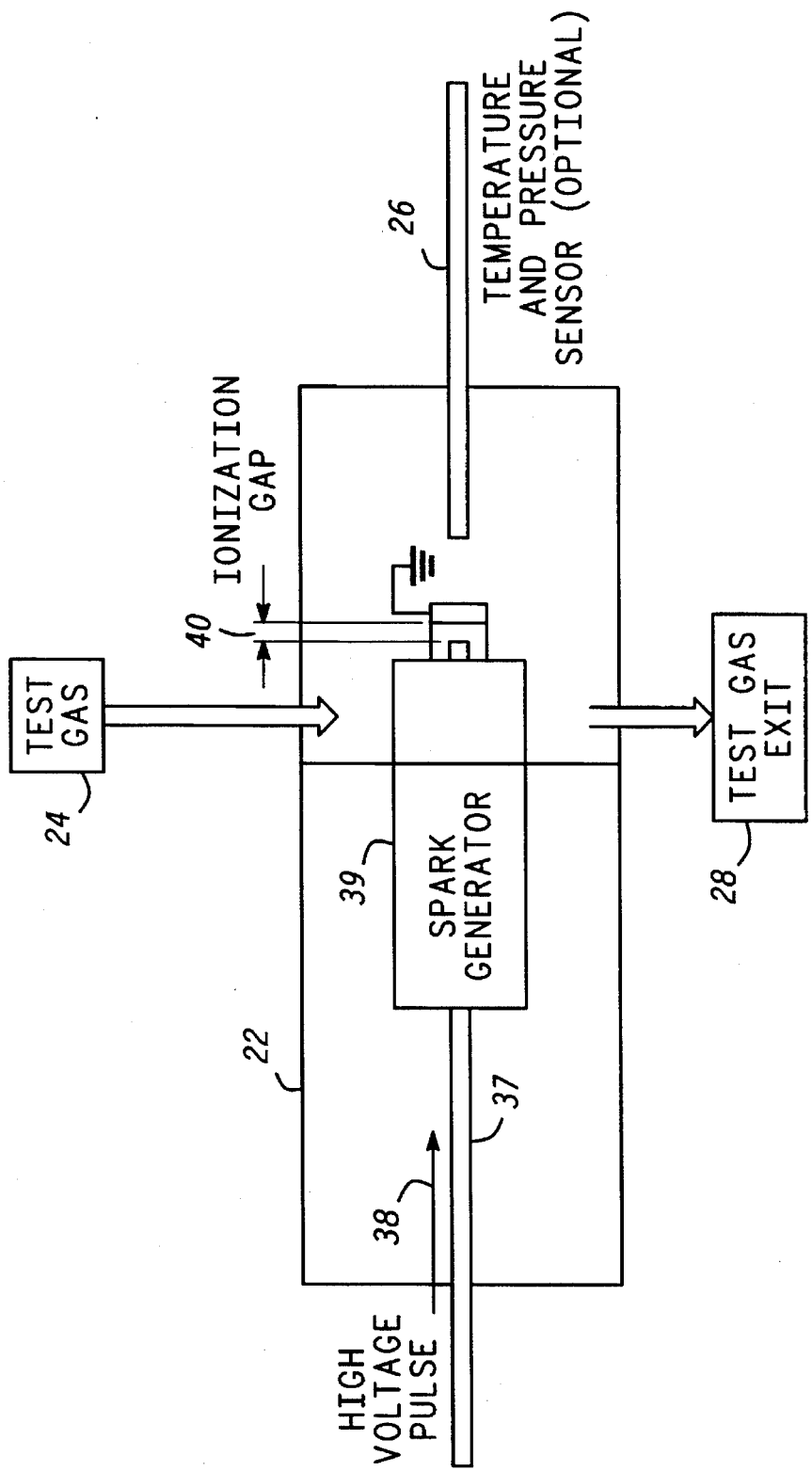
In FIG. 2, there is shown an ionization chamber and gas analyzer system in accordance with FIG. 1 and a preferred embodiment of the invention.

FIG. 2 illustrates the ionization chamber and gas analyzer 22 method and apparatus. Test gas 24, for which the ionization voltage is to be measured, is introduced into the ionization chamber and gas analyzer 22. Conventional means can be used as intake ports and exhaust ports for test gas 24 introduction into the ionization chamber 22 and test gas exit 28 from the ionization chamber 22. Other alternatives, e.g., can include the ionization chamber 22 as a region within the exhaust system of a motor vehicle. Such an exhaust system implementation could be run continually or periodically to monitor the exhaust gas concentration of the motor vehicle engine.

The high voltage pulse 38 of FIG. 2 is input to conductor 37 coupled to spark generator 39. Spark generator 39 can be any means for generating a spark, such as conventional spark plugs used in internal combustion engines. The electrode gap or ionization gap 40 in FIG. 2 can be varied and different electrode geometries and materials can be used. Four such spark plug arrangements were used in a preferred embodiment of the invention as built and tested. The first was a platinum tip ionizer spark plug with an electrode gap of approximately 2.67 millimeters (mm) (or 105 mils); the second was a metal alloy (refractive metal) with a modified gap of approximately 2.39 mm (or 94 mils); the third was a fine platinum wire ionizer with a gap of approximately 0.762 mm (or 30 mils); and, the fourth was a fine platinum wire with a modified gap ionizer with a gap of approximately 3.25 mm (or 128 mils). As an example, the spark plugs which were used in the device were Autolite Ap26, Champion N7YC, Bosch HR9-BP spark plugs.

The FIG. 2 illustration shows only one spark generator 38, when multiple spark generators, either within a single ionization chamber and gas analyzer 22, or in separate, multiple ionization chambers and gas analyzers (or a compartmentalized single ionization chamber) can be used simultaneously. FIG. 2 also shows the optional temperature and pressure sensor 26.

In function, the high voltage pulse 38 in FIG. 2 is input into the ionization chamber and gas analyzer 22 after test gas 24 is introduced into the ionization chamber and gas analyzer 22. The ionization test chamber and gas analyzer 22 uses the variation of the breakdown voltage of a gas, or mixture of gases, as the measured parameter to identify a gas species. Since the ionization energy, the number of secondary electrons emitted, and the cross section of gas molecules are different for different gas mixtures, the ionization voltage for avalanche ionization is also different. By measuring the avalanche ionization voltage and comparing it to calibrated data, gas type and concentration can be determined. By changing gap width, gap shape, surface metal of electrodes, etc. across multiple spark generator means (e.g. spark plugs), a set of different avalanche ionization voltages can be obtained with a set series of designs of gaps.

Figure 3:
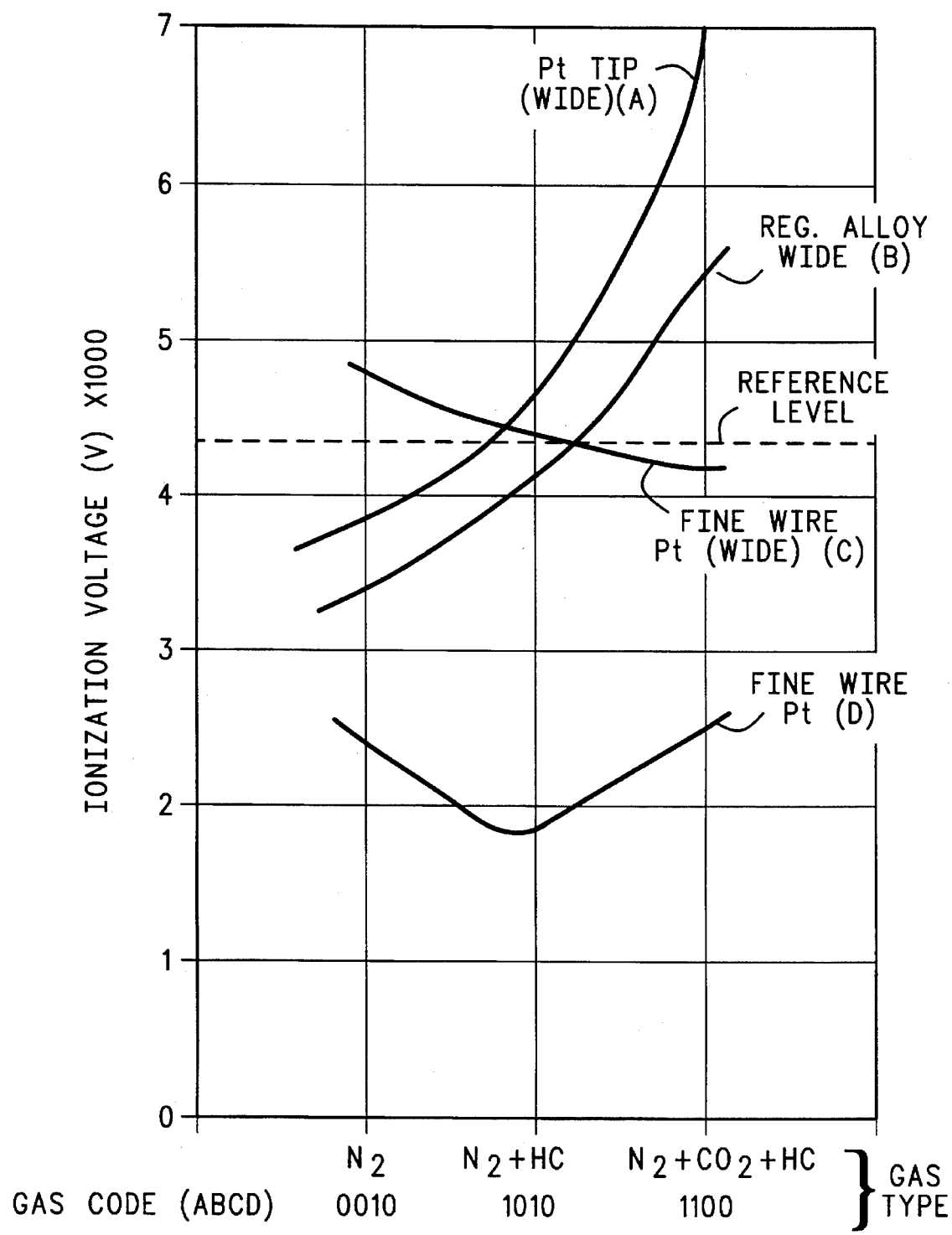
In FIG. 3, there is shown a graph of ionization voltages versus gas type in accordance with measurements made using the ionization gas analyzer system of FIGS. 1 and 2; and In FIG. 4, there is shown a graph of ionization gas analyzer test data representing ionization voltage versus gas concentration for propane.

In FIG. 3, there is shown a graph of ionization voltages versus gas type in accordance with measurements made using the ionization gas analyzer system of FIGS. 1 and 2. Four labeled curves indicate measured ionization voltages in kilovolts (kV) for three different gases or mixtures and the four spark plug electrode gaps described above. The gases or mixtures tested are nitrogen (labeled $N_2$), nitrogen plus hydrocarbons (labeled $N_2$+HC), and nitrogen plus carbon dioxide plus hydrocarbons (labeled $N_2$+$CO_2$+HC).

The lowest curve of the four in FIG. 3 (from just less than 2 kV to about 2.7 kV) represents the ionization voltages for using the fine platinum wire electrode. The curve which shows ionization voltage declining as the gas mixtures were changed from nitrogen to nitrogen plus hydrocarbons to nitrogen plus carbon dioxide plus hydrocarbons represents the ionization voltages for using the fine platinum wire electrode with the wider gap (ionization voltages from just under 5 kV to just over 4 kV). The other two curves represent the ionization voltages for the wide gap regular alloy spark plug (ionization voltages from just over 3 kV to about 5.6 kV), and the platinum tip wide gap spark plug (the higher ionization voltage curve of the latter two, with ionization voltages from about 3.6 kV to over 7 kV).

Various methods can be used to evaluate the measured ionization voltage data, including using an average value of the peak ionization voltage, area under the ionization voltage curve, or ionization voltage measured as a function of time. The ionization voltage values can be defined and recorded as either analog or digital signals for gas signature identification.

FIG. 3 illustrates one method for establishing a digital signature word to uniquely identify a test gas. FIG. 3 shows a dashed reference level which is indicated as about 4.3 kV. Such a level is set arbitrarily such that some ionization voltages produced exceed the reference level and some do not. For example, with the reference level chosen as shown in FIG. 3, only the ionization voltage for the fine platinum wire electrode (wide gap) exceeds the reference level in the case of nitrogen gas. As a second example, both the ionization voltages for the fine platinum wire (wide gap) and the platinum tip (wide gap) exceed the reference level for the nitrogen plus hydrocarbon gas mixture. If a number one (1) is used to denote an ionization voltage meeting or exceeding the reference level and a number zero (0) is used to denote an ionization voltage below the reference level, and four digits are used to signify results for the spark plugs used (in the order of platinum tip (wide gap) as A, regular allow (wide gap) as B, fine platinum wire (wide gap) as C, and fine platinum wire as D in the sequence ABCD), the signature of each gas or mixture shown in FIG. 3 is unique. For example, for nitrogen, the ABCD signature is 0010, for nitrogen plus hydrocarbons the signature is 1010, and for nitrogen plus hydrocarbons plus carbon dioxide the signature is 1100. If one of the input voltages is used as the reference level, the system is self-calibrated and long term drifting of the system will not be a problem.

Figure 4:
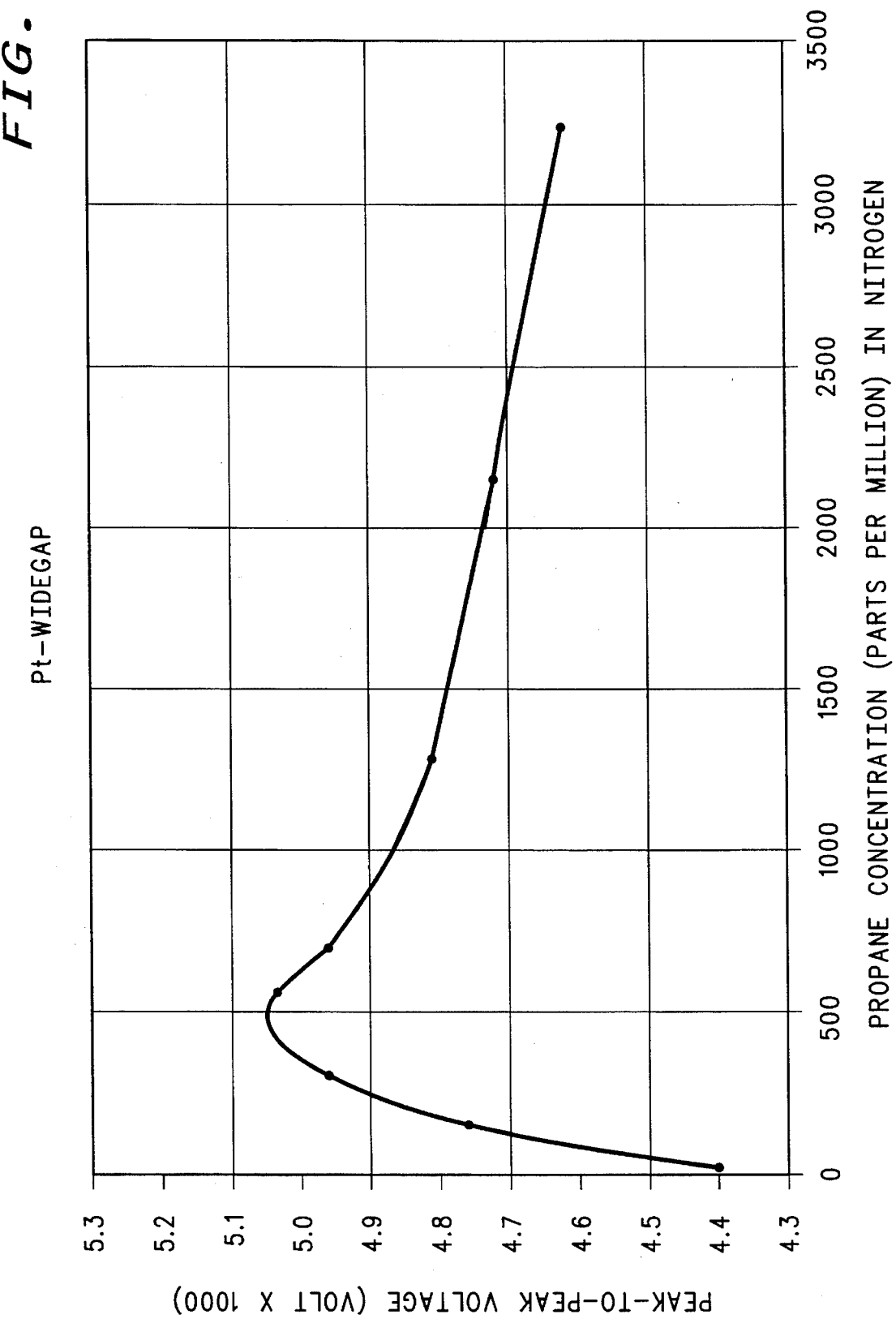

In FIG. 4, there is shown a graph of ionization gas analyzer test data representing ionization voltage versus gas concentration for propane (in parts per million) in nitrogen gas. The test data was taken using the platinum tip (wide gap) spark plug. Note that the variation of the ionization voltage with gas concentration shows that the above-described method and apparatus can also be used to differentiate among different concentrations of a constituent gas in a mixture. The same multiple ionization voltage curves in FIG. 3 can be generated to show variations based on gas concentration, as well as gas composition. The digital signature approach can thus be extended to distinguish among various concentration levels of gas, as well as different gas types. For increased precision of measuring concentration levels, more spark generators providing more ionization curves may be required.

Thus, an ionization gas analyzer system and method has been described which overcomes specific problems and accomplishes certain advantages relative to prior art methods and mechanisms. The improvements over known technology are significant.

Thus, there has also been provided, in accordance with an embodiment of the invention, an ionization gas analyzer system and method that fully satisfies the aims and advantages set forth above. While the invention has been described in conjunction with a specific embodiment, many alternatives, modifications, and variations will be apparent to those of ordinary skill in the art in light of the foregoing description. Accordingly, the invention is intended to embrace all such alternatives, modifications, and variations as fall within the spirit and broad scope of the appended claims.

What is claimed is:

1. An ionization gas analyzer system comprising:

an ionization chamber including a plurality of ionization electrodes contained therein, the ionization chamber containing a test gas;

a high voltage generator coupled to the plurality of ionization electrodes, the high voltage generator for providing a plurality of variable high voltage pulses to the plurality of ionization electrodes; and an ionization voltage analyzer coupled to the ionization chamber, wherein the ionization voltage analyzer receives a plurality of ionization voltages from the plurality of ionization electrodes in response to the plurality of variable high voltage pulses, and produces a gas code identifier in response thereto.

2. An ionization gas analyzer system as claimed in claim 1, wherein the ionization chamber further comprises a temperature and pressure sensor to monitor the temperature and pressure within the ionization chamber.

3. An ionization gas analyzer system as claimed in claim 1, wherein the plurality of ionization electrodes comprise spark plugs.

4. An ionization gas analyzer system as claimed in claim 1, wherein the high voltage generator comprises:

a power source;

a pulse generator for generating a voltage pulse;

a power switch coupled to the pulse generator and the power source, the power switch for providing power from the power source to the pulse generator;

a primary ignition coil coupled to the power switch, the primary ignition coil for receiving the voltage pulse; and a secondary ignition coil coupled to the primary ignition coil, the secondary ignition coil for producing a high voltage pulse in response to the voltage pulse in the primary ignition coil.

5. An ionization gas analyzer system as claimed in claim 1, wherein the ionization voltage analyzer comprises a voltage sensor for receiving the plurality of variable high voltage pulse from the high voltage generator and for receiving the plurality of ionization voltages from the ionization chamber.

6. An ionization gas analyzer system as claimed in claim 5, wherein the ionization voltage analyzer further comprises a scope coupled to the voltage sensor, wherein the scope monitors the plurality of ionization voltages.

7. An ionization gas analyzer system as claimed in claim 6, wherein the ionization voltage analyzer further comprises a computer coupled to the scope, wherein the computer analyzes the plurality of ionization voltages and produces the gas code identifier.

8. An ionization gas analyzer system as claimed in claim 7, wherein the ionization voltage analyzer further comprises a display coupled to the computer, wherein the display shows the gas code identifier.

9. A method for identifying gases using ionization voltage comprising the steps of:

providing an ionization chamber including a plurality of ionization electrodes therein;

providing a test gas within the ionization chamber;

providing a plurality of variable high voltage pulses to the plurality of ionization electrodes from a high voltage generator;

generating a plurality of ionization voltages from the plurality of variable high voltage pulses in an ionization voltage analyzer; and producing a gas code identifier from the ionization voltage analyzer in response to the plurality of ionization voltages.

10. A method as claimed in claim 9, wherein the step of providing a plurality of high voltage pulses comprises the steps of:

generating a voltage pulse in a pulse generator; and creating a high voltage pulse in response to the voltage pulse using a primary and a secondary ignition coil.

11. A method as claimed in claim 9, wherein the step of generating a plurality of ionization voltages from the plurality of variable high voltage pulses comprises the step of providing the plurality of ionization voltages to a plurality of spark plugs.

12. A method as claimed in claim 9, wherein the step of producing a gas code identifier from the ionization voltage analyzer in response to the plurality of ionization voltages comprises the step of monitoring the plurality of ionization voltages from the ionization chamber.

13. A method as claimed in claim 12, wherein the step of producing a gas code identifier from the ionization voltage analyzer in response to the plurality of ionization voltages further comprises the step of analyzing the plurality of ionization voltages in a computer.

14. A method as claimed in claim 13, wherein the step of analyzing the plurality of ionization voltages in a computer comprises the steps of:

setting a reference level ionization voltage; and comparing each of the plurality of ionization voltages to the reference level ionization voltage.

15. A method as claimed in claim 14, wherein the step of producing a gas code identifier comprises the step of defining a code based on the plurality of ionization voltages that exceed the reference level ionization voltage.

16. A motor vehicle having an exhaust gas analyzer system comprising:

an ionization chamber including a plurality of ionization electrodes contained therein, the ionization chamber containing a test gas;

a high voltage generator coupled to the plurality of ionization electrodes, the high voltage generator for providing a plurality of variable high voltage pulses to the plurality of ionization electrodes; and an ionization voltage analyzer coupled to the ionization chamber, wherein the ionization voltage analyzer receives a plurality of ionization voltages from the plurality of ionization electrodes in response to the plurality of variable high voltage pulses, and produces a gas code identifier in response thereto.

17. A motor vehicle as claimed in claim 16, wherein the ionization chamber further comprises a temperature and pressure sensor to monitor the temperature and pressure within the ionization chamber.

18. A motor vehicle as claimed in claim 16, wherein the plurality of ionization electrodes comprise spark plugs.

19. A motor vehicle as claimed in claim 16, wherein the high voltage generator comprises:

a power source;

a pulse generator for generating a voltage pulse;

a power switch coupled to the pulse generator and the power source, the power switch for providing power from the power source to the pulse generator;

a primary ignition coil coupled to the power switch, the primary ignition coil for receiving the voltage pulse; and a secondary ignition coil coupled to the primary ignition coil, the secondary ignition coil for producing a high voltage pulse in response to the voltage pulse in the primary ignition coil.

20. A motor vehicle as claimed in claim 16, wherein the ionization voltage analyzer comprises a voltage sensor for receiving the plurality of variable high voltage pulses from the high voltage generator and for receiving the plurality of ionization voltages from the ionization chamber.

21. A motor vehicle as claimed in claim 20, wherein the ionization voltage analyzer further comprises a scope coupled to the voltage sensor, wherein the scope monitors the plurality of ionization voltages.

22. A motor vehicle as claimed in claim 21, wherein the ionization voltage analyzer further comprises a computer coupled to the scope, wherein the computer analyzes the plurality of ionization voltages and produces the gas code identifier.

23. A motor vehicle as claimed in claim 22, wherein the ionization voltage analyzer further comprises a display coupled to the computer, wherein the display shows the gas code identifier.

* * * * *